(12) United States Patent
Dhanoa

(10) Patent No.: US 8,530,479 B2
(45) Date of Patent: Sep. 10, 2013

(54) DEUTERIUM-ENRICHED ALKYL SULFONAMIDES

(76) Inventor: Daljit Singh Dhanoa, Del Mar, CA (US)

( * ) Notice: Subject to any disclaimer, the term of this patent is extended or adjusted under 35 U.S.C. 154(b) by 373 days.

(21) Appl. No.: 12/806,279

(22) Filed: Aug. 9, 2010

(65) Prior Publication Data

US 2011/0034479 A1  Feb. 10, 2011

Related U.S. Application Data

(60) Provisional application No. 61/273,767, filed on Aug. 10, 2009.

(51) Int. Cl.
*A61K 31/4965* (2006.01)
*C07D 295/135* (2006.01)

(52) U.S. Cl.
USPC ..................... 514/255.03; 544/393

(58) Field of Classification Search
USPC ..................... 514/255.03; 544/393
See application file for complete search history.

(56) References Cited

U.S. PATENT DOCUMENTS 7,153,858 B2 * 12/2006 Dhanoa et al. ........... 514/253.01

FOREIGN PATENT DOCUMENTS

WO    WO 9526325    * 10/1995

OTHER PUBLICATIONS

Kushner et al., Pharmacological uses and perspectives of heavy water and deuterated compounds, 1999, Can. J. Physiol. Pharmacol., 77, 79-88.*

* cited by examiner

*Primary Examiner* — Kristin Vajda
(74) *Attorney, Agent, or Firm* — Karl Heidert

(57) ABSTRACT

The present invention is concerned with deuterium-enriched isobutyl and cyclohexylmethyl sulfonamides of formula I and II, and pharmaceutically acceptable salts and methods of use thereof for the treatment of general anxiety disorders, major depressive disorders, attention deficit disorders, attention deficit hyperactivity disorder, Alzheimer's disease, fronto-temporal dementia, cognitive impairment associated with age-related dementia, schizophrenia, migraine, sleep disorders, neurodegenerative diseases and obesity.

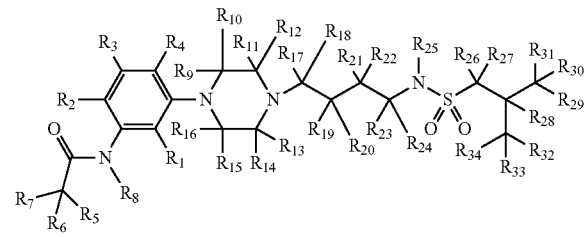

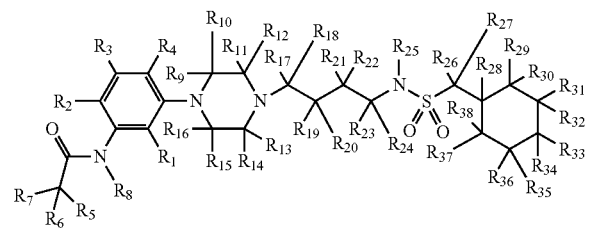

7 Claims, No Drawings

DEUTERIUM-ENRICHED ALKYL SULFONAMIDES

CROSS-REFERENCE TO RELATED APPLICATIONS

The present application claims priority benefit under 35 U.S.C. article section 119 (e) of U.S. Provisional Patent Application Ser. No. 61/273,767 filed Aug. 10, 2009. The disclosure of this application is incorporated herein by reference.

FIELD OF THE INVENTION

The present invention is generally related to deuterium-enriched N-acetylamino-(piperazinyl)-butyl)-isobutylsulfonamide [also named as N-(isobutyl-sulfonylamino-butyl-piperazin-1-yl)phenyl)-acetamides] and N-acetylamino-(piperazinyl)-butyl)-cyclohexylmethylsulfonamide [also named as N-(cyclohexylmethyl-sulfonylamino-butyl-piperazin-1-yl)phenyl)-acetamides] their deuterium enriched derivatives of formula I and formula II, pharmaceutically acceptable salts thereof, synthesis and methods of use thereof. These compounds are 5-$HT_{1A}$ (5-hydroxytryptamine or serotonin) receptor agonists or partial agonists or antagonists and are useful as therapeutic agents for the treatment of general anxiety disorders, major depressive disorders, attention deficit disorders, attention deficit hyperactivity disorder, Alzheimer's disease, frontotemporal dementia, cognitive impairment associated with age-related dementia, schizophrenia, migraine, sleep disorders, neurodegenerative diseases, obesity and Huntington disease.

SUMMARY OF THE INVENTION

The present invention is concerned with deuterium-enriched isobutyl and cyclohexylmethyl sulfonamides of formula I and II, and pharmaceutically acceptable salts and methods of use thereof,

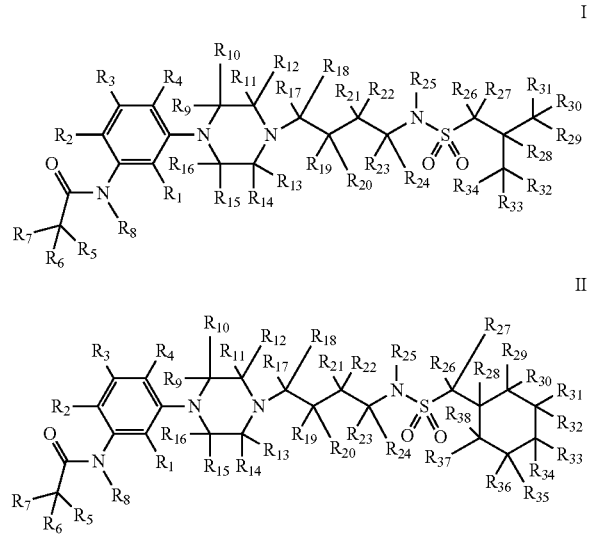

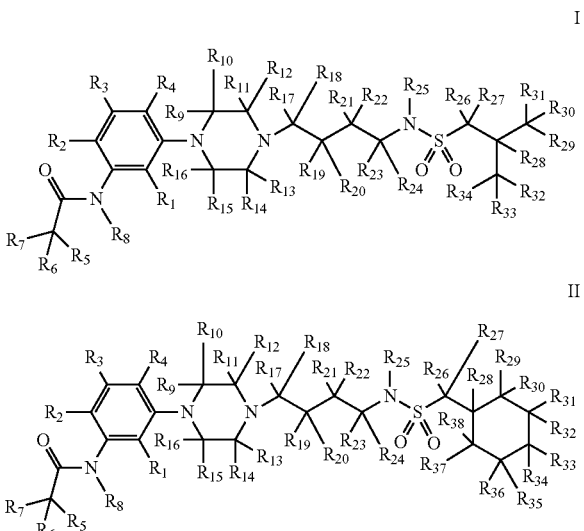

wherein:
$R_1$ to $R_{34}$ are independently D and H;
$R_{25}$ is D, $CD_3$;

for the treatment of general anxiety disorders, major depressive disorders, attention deficit disorders, attention deficit hyperactivity disorder, Alzheimer's disease, frontotemporal dementia, cognitive impairment associated with age-related dementia, schizophrenia, migraine, sleep disorders, neurodegenerative diseases and obesity.

One object of the present invention is to provide deuterium-enriched N-(isobutyl-(N-methyl-sulfonylamino-butyl-piperazin-1-yl)phenyl)-acetamides or a pharmaceutically acceptable salt thereof.

One object of the present invention is to provide deuterium-enriched N-(cyclohexylmethyl-(N-methyl-sulfonylamino-butyl-piperazin-1-yl)phenyl)-acetamides or a pharmaceutically acceptable salt thereof.

It is another object of the present invention to provide pharmaceutical compositions comprising pharmaceutically acceptable carrier and a therapeutically effective amount of at least one of the deuterium-enriched compounds of the present invention or a pharmaceutically acceptable salt thereof.

It is another object of the present invention to provide a method for treating anxiety, generalized anxiety disorder, depression, major depressive disorder, attention deficit disorder, attention deficit hyperactivity disorder, comprising administration to a host in need of such treatment a therapeutically effective amount of at least one of the deuterium-enriched compounds of the present invention or a pharmaceutically acceptable salt thereof.

It is another object of the present invention to provide a method for treating Alzheimer's Disease, frontotemporal dementia, Huntington's disease, cognitive and/or memory impairment (or dysfunction) associated with schizophrenia, and age-related dementia, sleep disorders, migraine, obesity, comprising administration to a host in need of such treatment a therapeutically effective amount of at least one of the deuterium-enriched compounds of the present invention or a pharmaceutically acceptable salt thereof.

It is another object of the present invention to provide a method for treating migraine, sleep disorder, and pain, comprising administration to a host in need of such treatment a therapeutically effective amount of at least one of the deuterium-enriched compounds of the present invention or a pharmaceutically acceptable salt thereof.

It is another object of the present invention to provide a novel deuterium-enriched isobutylsulfonamide and cyclohexylmethylsulfonamide derivatives of formula I and II or a pharmaceutically acceptable salt thereof for use as a therapeutic in the treatment of anxiety, generalized anxiety disorder, depression, major depressive disorder, attention deficit disorder, attention deficit hyperactivity disorder, comprising administration to a host in need of such treatment a therapeutically effective amount of at least one of the deuterium-enriched compounds of the present invention or a pharmaceutically acceptable salt thereof.

It is another object of the present invention to provide the use of a novel deuterium-enriched compounds of this invention of formula I and II or a pharmaceutically acceptable salt thereof for the manufacture of a medicament (e.g., for the treatment of generalized anxiety disorder, major depressive disorder, attention deficit disorder, attention deficit hyperactivity disorder, obesity, Alzheimer's disease, cognitive impairment associated with age-related dementia, frontotemporal dementia, schizophrenia, migraine, sleep disorders and obesity).

BACKGROUND OF THE INVENTION

Neurotransmitter serotonin or 5-Hydroxytryptamine (5-HT) is abundantly distributed in the central nervous system, including hippocampus and frontal cortex. 5-HT receptors are a family of G-protein coupled receptors, characterized with 7-transmembrane helices and presently have fourteen known receptor subtypes, some of which exist as multiple splice variants [D. L. Murphy, A. M. Andrews, C. H. Wichems, Q. Li, M. Tohda and B. Greenberg, *J. Clin. Psychiatry,* 1998, 59 (suppl. 15), 4]. 5-HT influences a number of physiological functions and is implicated in a large number of central nervous system disorders and neurodegenerative diseases [W. E. Childers, Jr. and A. J. Robichaud, *Ann. Rep. Med. Chem.* 2005, 40, 17].

One of the most actively studied 5-HT receptor subtypes is 5-HT$_{1A}$, a 421 amino acid protein coded on human chromosome 5 by an intronless gene. 5-HT$_{1A}$ receptors are expressed in the central nervous system with highest density in the dorsal and median raphe nuclei as well as in the hippocampus. High density is also seen in the frontal cortex, entorhinal cortex, amygdale, and septum. 5-HT$_{1A}$ agonists and partial agonists have been implicated I and have demonstrated effectiveness in the treatment of anxiety and depression in the clinic. Partial agonists of the 5-HT$_{1A}$ receptor mediate antidepressant activity through an increase in serotonergic neurotransmission. Although the mechanism of action is not yet fully understood, there is substantial evidence that the physiological and behavioral responses are achieved following desensitization of the 5-HT$_{1A}$ receptor-mediated response.

According to the U.S. National Institute of Mental Health, generalized anxiety disorder and depression are the most prevalent mental illnesses. Most of the drugs used for treating anxiety and depression suffer from troublesome side effects. Selective serotonin reuptake inhibitors (SSRIs) and the more recently developed serotonin nonadrenaline reuptake inhibitors (SNRIs) exert their effects by increasing neurotransmitter availability and transmission. Another class of drugs used for the short-term relief of anxiety is benzodiazepines. These sedating agents are controlled substances because of their addictive properties and can be lethal when used in combination with alcohol.

The 5-HT$_{1A}$ agonists are safer and more effective therapeutic drugs for the treatment of anxiety and depression and potentially useful in the treatment of other CNS diseases including Alzheimer's, cognitive and memory dysfunction, frontotemporal dementia, sleep disorders, cognitive impairment associated with schizophrenia, pain, migraine, obesity and Huntington's disease,

DETAILED DESCRIPTION OF THE INVENTION

The present invention relates to deuterium-enriched N-(isobutyl and cyclohexyl-sulfonylamino-butyl-piperazin-1-yl)phenyl)-acetamides and their deuterium enriched derivatives as shown in formula I and formula II, their pharmaceutically acceptable salts, compositions and their use as therapeutic agents for the prevention and treatment of anxiety, generalized anxiety disorder, depression, major depressive disorder, attention deficit disorder, attention deficit hyperactivity disorder, migraine, Alzheimer's disease, cognitive and memory impairment associated with schizophrenia and other age-related dementia, frontotemporal dementia, obesity, migraine and sleep disorders and Huntington's disease.

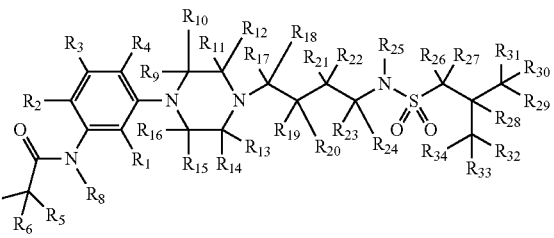

I

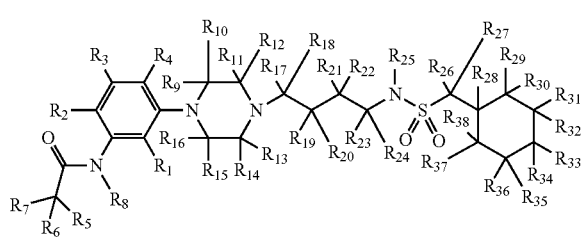

II

Deuterium (D or $^2$H) is a stable isotope non-radioactive isotope of hydrogen (H) and has an atomic weight of 2.0144. Hydrogen occurs naturally as a mixture of the isotopes $^1$H, D ($^2$H), and T ($^3$H or tritium) and the natural abundance of deuterium is 0-015%. One of ordinary skill in the art recognizes that in all compounds containing H atom, H actually represents a mixture of H and D, with about 0-015% of D. So, compounds with a level of D that have been enriched to be greater than its natural abundance of 0.015%, should be considered unnatural and as a result novel as compared to their corresponding non-enriched counterparts.

The carbon-hydrogen bonds contain a naturally occurring distribution of hydrogen isotopes, namely $^1$H or protium (about 99.9844%), $^2$H or deuterium (D) (about 0.0156%), and $^3$H or tritium (in the range between about 0.5 and 67 tritium atoms per $10^{18}$ protium atoms). Higher levels of deuterium incorporation produce a detectable Kinetic Isotope Effect (Werstiuk, N. H.; Dhanoa, D. S.; Timmins, G. Can J. Chem. 1979, 57, 2885; Werstiuk, N. H.; Dhanoa, D. S.; Timmins, G. *Can J. Chem.* 1983, 61, 2403), that could improve the pharmacokinetic, pharmacologic and/or toxicologic parameters of compounds of formula I and II in comparison to compounds having naturally occurring levels of deuterium and their corresponding hydrogen (protium) analogs. The present invention disclosed herein describes novel compounds of formula I and II containing higher content of deuterium (>1%), synthesis and uses thereof for the treatment of central nervous system diseases including anxiety, generalized anxiety disorder, depression, major depressive disorder, attention deficit disorder, attention deficit hyperactivity disorder, Alzheimer's disease, Huntington's disease, cognitive and memory impairment associated with schizophrenia and other age-related dementia migraine, sleep disorders, neural injury and stroke.

Suitable modifications of certain carbon-hydrogen bonds into carbon-deuterium bonds may generate novel substituted compounds of formula I and II with unexpected and non-obvious improvements of pharmacological, pharmacokinetic and toxicological properties in comparison to the non-isotopically enriched dimebon. This invention relies on the judicious and successful application of chemical kinetics to drug design. Deuterium incorporation levels in the compounds of the invention are significantly higher than the naturally-occurring levels and are sufficient to induce at least one substantial improvement as described herein. All percentages given for the amount of D present are mole percentages.

Deuterium enrichment" refers to the percentage of incorporation of deuterium at a given site on the molecule instead of a hydrogen atom. For example, deuterium enrichment of 1% means that in 1% of molecules in a given sample a particular site is occupied by deuterium. Because the naturally occurring distribution of deuterium is about 0.0156%, deuterium enrichment in compounds synthesized using non-enriched starting materials is about 0.0156%.

It can be a significant synthetic challenge to produce 100% deuterium at a specific site of a compound. When 100% deuteration is recited or a deuterium atom is specifically shown in a chemical structure of a compound, a small amount of deuterium may still be present. Higher levels of deuterium content in a compound can be produced either by Hydrogen-Deuterium (H-D) exchange or by synthesizing the compound for specific deuteration. The H-D exchange is readily achieved in case of H atoms attached to heteroatoms for example in cases of carboxylic acids ($CO_2H$), amides, CONHR, sulfonamides ($SO_2NH_2$), alcohols (OH), basic amines (NH2), etc. However, these incorporated D attached to hetero atoms (O, N, S) etc, readily revert back to H upon exposure to water or any acidic compounds containing H atoms. The preferred deuterium containing compounds are the ones which contain D directly attached to carbon atoms of the structure of the compounds of this invention.

In some embodiments, the deuterium enrichment in the compounds of the present invention is greater than 4%, 5%, 6%, 7%, 8%, 9% or 10%. In other embodiments, the deuterium enrichment in the compounds of the present invention is greater than 20%. In further embodiments, the deuterium enrichment in the compounds of the present invention is greater than 50%. In some embodiments, the deuterium enrichment in the compounds of the present invention is greater than 70%. In some embodiments, the deuterium enrichment in the compounds of the present invention is greater than 90%.

This invention is concerned with deuterium-enriched compounds of structural formula I and II, derivatives thereof and pharmaceutically acceptable salts and compositions thereof,

I

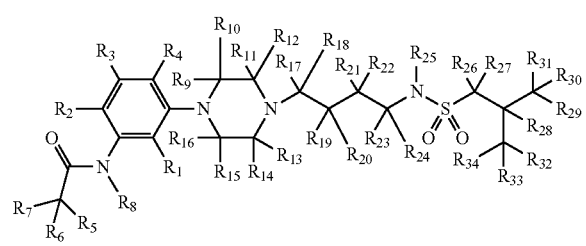

-continued

II

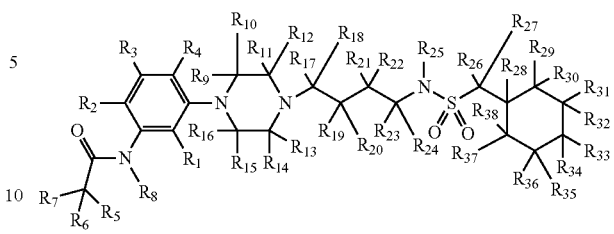

wherein:

$R_1$-$R_{34}$ in formula I are independently H, D, $CD_3$, $CDH_2$, $CD_2H$, (wherein D is Deuterium atom present in the compounds of formula I, 1%-100% enrichment of deuterium is incorporated);

$R_1$-$R_{38}$ in formula II are independently H, D, $CD_3$, $CDH_2$, $CD_2H$, F, Cl (wherein D is Deuterium atom present in the compounds of formula II, 1%-100% enrichment of deuterium is incorporated);

$R_{25}$ is D, $CD_3$, H;

In another embodiment, the present invention provides a novel, deuterium enriched compound of formula I or a pharmaceutically acceptable salt thereof, wherein at least one or all of the H atoms are substituted with D (deuterium atom) and the abundance of deuterium incorporated in the compounds is at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 365, 37%, 38%, 39%, 40%, 41%, 42%, 43%, 44%, 45%, 46%, 47%, 48%, 49%, 50%, 51%, 52%, 53%, 545, 55%, 56%, 57%, 58%, 59%, 60%, 61%, 62%, 63%, 64%, 65%, 66%, 67%, 68%, 69%, 70%, 71%, 72%, 73%, 74%, 755, 76%, 77%, 78%, 79%, 80%, 81%, 81%, 83%, 84%, 85%, 86%, 87%, 88%, 89%, 90%, 91%, 92%, 93%, 94%, 95%, 96%, 97%, 98%, 99% and 100%.

In another embodiment, the present invention provides a novel, deuterium enriched compound of formula II or a pharmaceutically acceptable salt thereof, wherein at least one or all of the H atoms are substituted with D (deuterium atom) and the abundance of deuterium incorporated in the compounds is at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 365, 37%, 38%, 39%, 40%, 41%, 42%, 43%, 44%, 45%, 46%, 47%, 48%, 49%, 50%, 51%, 52%, 53%, 545, 55%, 56%, 57%, 58%, 59%, 60%, 61%, 62%, 63%, 64%, 65%, 66%, 67%, 68%, 69%, 70%, 71%, 72%, 73%, 74%, 755, 76%, 77%, 78%, 79%, 80%, 81%, 81%, 83%, 84%, 85%, 86%, 87%, 88%, 89%, 90%, 91%, 92%, 93%, 94%, 95%, 96%, 97%, 98%, 99% and 100%.

The present invention provides an amount of a novel deuterium-compound of formula I and formula II.

Examples of amounts include, but are not limited to (a) at least 0.01, 0.02, 0.03, 0.04, 0.05, 0.1, 0.2, 0.3, 0.4, 0.5, to 1 mole, (b) at least 0.1 mole, and (c) at least 1 mole of the compound I or of compounds II. The present amounts also cover lab-scale (e.g., gram scale), kilo-lab scale, and industrial or commercial scale (e.g., multi-kilogram or larger scale) quantities as these will be more useful in the actual manufacture of a pharmaceutical, industrial/commercial scale refers to the amount of product that would be produced in a batch that was designed for clinical testing, formulation, sale/distribution to the public, etc.

In another embodiment, the present invention provides a novel, deuterium enriched compound of formula I or II or pharmaceutically acceptable salt thereof.

In another embodiment, the present invention provides a novel, deuterium enriched compound of formula I and formula II or a pharmaceutically acceptable salt thereof, wherein abundance of deuterium at each carbon center is at least 5%, 10%, 15%, 20%, 25%, 30%, 40%, 50%, 60% 70%, 80%, 90% and 100%.

In another embodiment, the present invention provides a novel method for treating general anxiety disorder, major depressive disorder, Alzheimer's disease, Huntington's disease, cognitive and memory impairment (or dysfunction) associated with schizophrenia or age-related dementia, frontotemporal dementia, migraine, pain, sleep disorders, neural injury and stroke, comprising: administering to a patient in need thereof a therapeutically effective amount of a deuterium-enriched compound of the present invention.

In another embodiment, the present invention provides the use of an amount of deuterium-enriched compound of the present invention for the manufacture of a medicament (e.g., for the treatment of Alzheimer's Disease, Huntington's disease, cognitive and memory impairment (or dysfunction) associated with schizophrenia, and age-related dementia, obesity, migraine, and sleep disorders).

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

DEFINITIONS

The examples provided in the definitions present in this application are non-inclusive unless otherwise stated. They include but are not limited to recited examples. The compounds of the present may have various isomers including all stereoisomers of asymmetric atoms and geometric, tautomeric or rotamers, and all isomers are considered to be part of the present invention. All processes used to prepare compounds of the present invention and intermediates made therein are considered to be part of the present invention.

"Therapeutically effective amount" includes an amount of a compound of the present invention that is effective when administered alone or in combination to treat the desired condition or disorder. "Therapeutically effective amount" includes an amount of the combination of compounds claimed that is effective to treat the desired condition or disorder. The combination of compounds is preferably a synergistic combination.

"Pharmaceutically acceptable salts" refer to derivatives of the disclosed compounds wherein the parent compound is modified by making acid or base salts thereof. Examples of the pharmaceutically acceptable salts include, but not limited to, mineral or organic acid salts of the basic residues. The pharmaceutically acceptable salts include but not limited to HCl, DCl, HBr, DBr, HI, DI, acetic, trifluoroacetic, citric, ascorbic, benzoin, methanesulfonic, benzenesulfonic, bicarbonic, carbonic, ethane disulfonic, edetic, fumaric, maleic, lactic, malic, mandelic, gluconic, glutamic, glycolic, glycollyarsanilic, lauryl, hexylresorcinic, hyrdabamic, hydroxymaleic, hydroxynaphthoic, isethionic, lactobionic, napsylic, nitric, oxalic, pamoic, pantothenic, phenyllacetic, phosphoric, polygalacturonic, propionic, salicyclic, stearic, subacetic, succinic, sulfamic, sulfanilic, sulfuric, tannic, tartaric, toluenesulfonic, and p-bromobenzenesulfonic.

The preparation of deuterated sulfonamide compounds of formula I and II are illustrated in schemes 1-6 below and in the examples given in Table 1. The schemes and examples are given for the purpose of illustrating the invention and not for limiting the scope or spirit of the invention.

Preparation of Deuterated Isobutylsulfonamide 10

Preparation of 3-N-Acetyl($d_3$)-Aniline 2

1,3-Diaminobenzene 1 is converted to 2 by selective monoacetylation with deuterated acetyl chloride ($CD_3COCl$) or deuterated acetic anhydride as illustrated in scheme 1 below. To a solution of 1 (5 g) in dicholoromethane or acetonitrile is added acetyl chloride-$d_3$ (1 equiv) at 0° C. and the mixture stirred for 1 hour. The reaction mixture is poured onto ice water and extracted with methylene chloride and washed with saturated aqueous solution of sodium bicarbonate. The organic phase is dried over anhydrous sodium sulfate, filtered, concentrated in vacuo and the product isolated by purification by flash chromatography to give 2 (4.5 g).

Preparation of Deuterated 3-N-Acetyl($d_3$)-Aniline (2,4,6 $d_3$) 3

To a mixture of 2 (1 g) and deuterated water $D_2O$ (2 ml) is added concentrated hydrochloric acid (HCl) (1 ml) and the reaction mixture is heated in microwave at 180° C. for 30 min. The mixture is allowed to attain room temperature and diluted with dichloromethane (100 ml). The mixture is cooled to 0° C. and saturated aqueous solution of sodium bicarbonate is added slowly to neutralize the reaction mixture. The organic phase is washed with saturated solution of sodium chloride (brine) and the organic phase is dried over sodium sulfate and filtered. The filterate is concentrated in vacuo to yield 3 (0.85 g). Mass spectral analysis: m/e 157 (M+1).

Preparation of 3-N-Acetyl($d_3$)-aminophenyl($d_3$)-piperazine 5

To a mixture of 3 (0.85 g) and potassium carbonate (3 equiv) in 1-butanol is added deuterated or undeuterated bis(2-chloroethyl)amine 4 (1 equiv) and the mixture refluxed for 24 hours. The mixture is allowed to cool down to room temperature and diluted with dichloromethane. The mixture is made alkaline by adding aqueous solution of NaOH. The mixture is then extracted with more dichloromethane, dried over anhydrous sodium sulfate, filtered, and the filtrate concentrated in vacuo. The product isolated by flash chromatography to give 5 (0.9 g).

Preparation of 3-N-Acetyl($d_3$)-aminophenyl($d_3$)-4-N-Boc-(aminobutyl)piperazine 7

A mixture of 5 (0.9 g), triethylamine (1.5 equiv) and N-Boc-butyl tosylate 6 (1.1 equiv) in acetonitrile is stirred for 24 hours. The mixture is diluted with dichloromethane and ice-water and stirred. The mixture is further treated with saturated aqueous solution of sodium hydroxide, stirred and the organic phase separated. The organic phase is dried over anhydrous sodium sulfate, filtered and the filtrate is concentrated in vacuo to give 7 (0.1.25 g) after flash chromatography.

Preparation of 3-N-Acetyl($d_3$)-aminophenyl($d_3$)-4-N-Boc-(aminobutyl)piperazine 8

To a solution of 7 (1.25 g) in dichloromethane at 0° C. is added trifluoroacetic acid (3 equiv) and the reaction mixture stirred for one and a half hour. The volatiles are removed in vacuo and the resulting precipitate is washed with diethyl ether and the precipitate is dried to yield 8 (0.85 g). Mass spectral analysis (m/e): 297 (M+1).

The N-Boc protection group is also removed by treatment of 7 with Hydrochloric acid in dioxane (HCl, dioxane).

Preparation of Deuterated N-[3-{4-(4-(2-Methyl($d_3$)-propan($d_7$)-1-sulfonylamino)-butyl)-piperazin-1-yl}-phenyl($d_3$)]acetamide($d_3$) 10

To a solution of the amine 8 (0.45 g) in dichloromethane at 0° C. is added deuterated isobutyl($d_9$)-sulfonyl chloride 9 (1 equiv) and the reaction mixture stirred for 4 hours. The mixture is concentrated by removing volatiles in vacuo, then diluted with dichloromethane and washed with aqueous sodium bicarbonate solution and then water. The organic phase is dried over sodium sulfate, then filtered and the filtrate concentrated. The resulting residue is flash chromatographed to give the target product 10 (0.50 g). Mass spectral analysis: (m/e) 426 (M+1).

Preparation of Deuterated N-[3-{4-(4-(cyclohexyl-methanesulfonylamino-butyl)-piperazin-1-yl]-phenyl ($d_3$)]-acetamide($d_3$) 12

To a solution of the amine 8 (0.4 g) in dichloromethane at 0° C. is added deuterated cyclohexylmethyl($d_{10}$)-sulfonyl chloride 11 (1 equiv) and the reaction mixture stirred for 4 hours. The mixture is concentrated in vacuo, then diluted with dichloromethane and washed with aqueous sodium bicarbonate solution and then water. The organic phase is dried over sodium sulfate, then filtered and the filtrate concentrated. The resulting residue is flash chromatographed to give the target product 12 (0.54 g). Mass spectral analysis: (m/e) 470 (M+1).

SCHEME 1

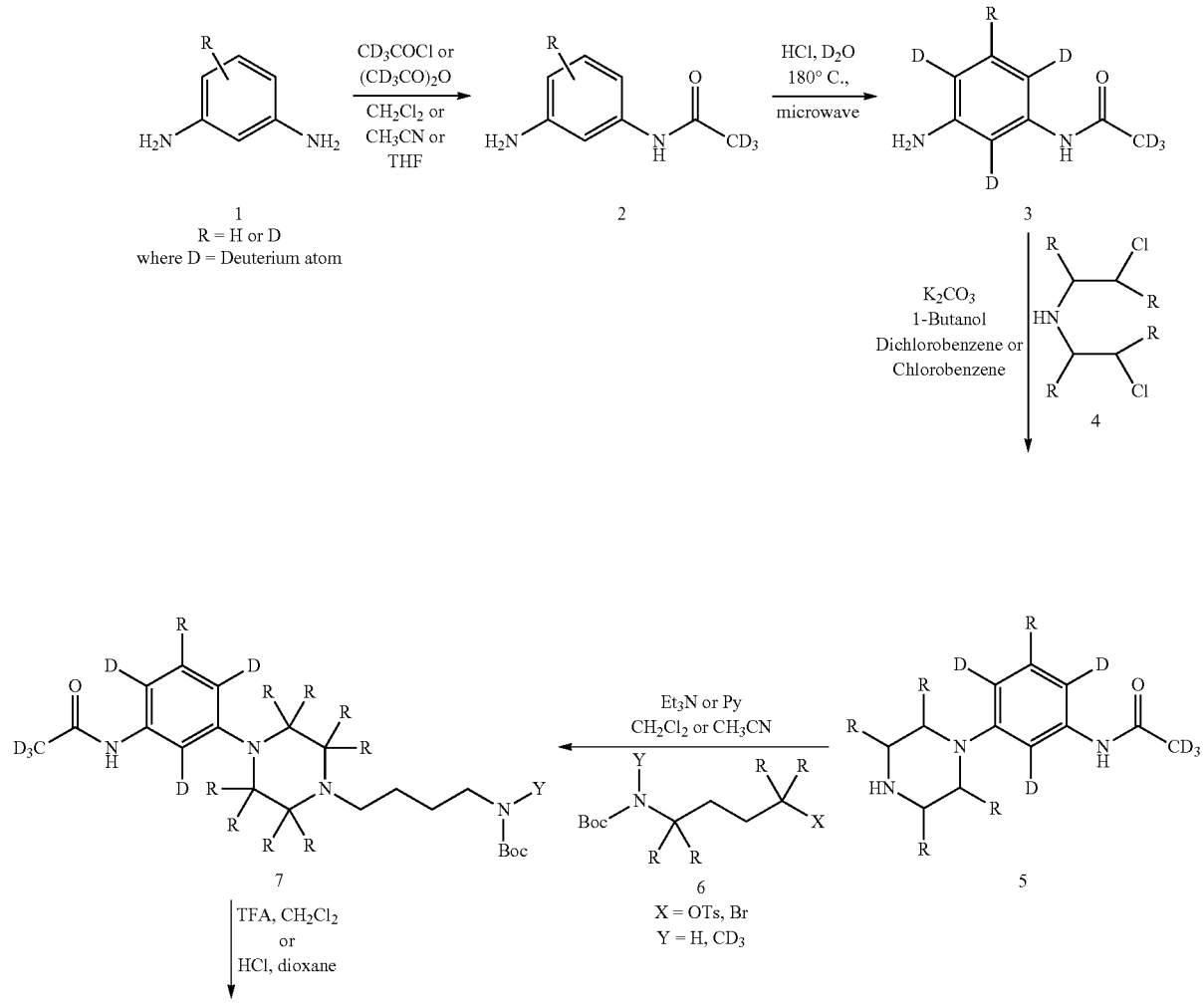

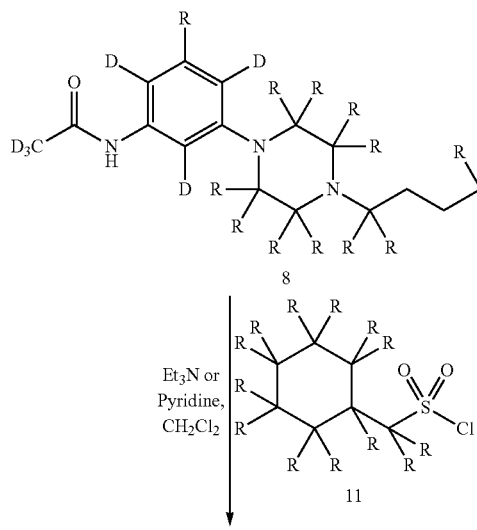
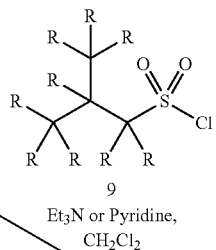
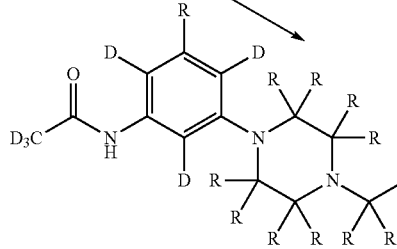

10
Y = H, D, CD$_3$
R = H, D

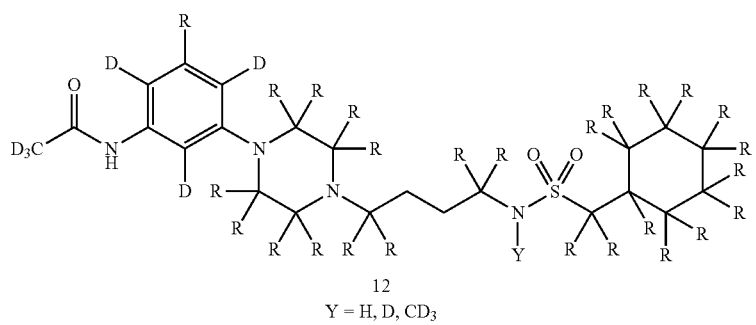

12
Y = H, D, CD$_3$
R = H, D

Preparation of isobutyl sulfonamide 10 and cyclohexylmethyl sulfonamide 12 from an alternative starting material 3-nitroanile is illustrated in scheme 2 and described below.

Preparation of Deuterated 3-Nitro-aniline-(d$_3$) 14

Deuterated 3-Nitro-aniline (2,4,6-d$_3$) 14 (1.2 g) is prepared from 3-nitroaniline 13 (1.5 g) by heating with D$_2$O and conc. HCl in microwave at 180° C. for 30 min as shown in scheme 2. Mass spectral analysis: m/e 142 (M+1). The method is described above for the preparation of 3 in scheme 1.

Preparation of Deuterated 3-Nitrophenyl(d$_3$)-piperazine 15

3-Nitro-aniline (d$_3$) 14 (1.2 g) is converted to 3-nitrophenyl (d3)-piperazine 15 (1.3 g) by refluxing in butanol with potassium carbonate and bis(chloroethyl)amine 4 for 36 hours as described for the preparation of 5. Mass spectral analysis: m/e 211 (M+1).

Preparation of 3-Nitrophenyl(d$_3$)amino-4-N-Boc-(aminobutyl)piperazine 16

15 (1.3 g) was converted to 16 (1.7 g) by alkylating with 6 (1 equiv) in dichloromethane and triethylamine as described above for the preparation of 7. Mass spectral analysis: m/e 382 (M+1).

Preparation of 3-Nitrophenyl(d$_3$)-4-piperazinyl-butylamine 17

The amine 17 (1.2 g) is prepared from the corresponding N-Boc derivative 16 (1.7 g) by TFA in dichloromethane as described above in the preparation of 8. Mass spectral analysis: m/e 282 (M+1).

Preparation of Deuterated 3-Nitrophenyl(d$_3$)-piperazinyl-4-n-butyl-isobutylsulfonamide 18

The amine 17 (0.6 g) is converted to the sulfonamide 18 (0.65 g) by treating with isobutylsulfonyl chloride 9 in dichloromethane and triethylamine as described above for the preparation of the sulfonamide 10. Mass spectral analysis: m/e 411 (M+1).

Preparation of Deuterated 3-Nitrophenyl(d$_3$)-piperazinyl-4-n-butyl-cyclohexylmethylsulfonamide 19

Similarly the amine 17 (0.5 g) is converted to the deuterated cyclohexylmethyl sulfonamide 19 (0.6 g) as described for the preparation of the sulfonamide 12.

Preparation of Deuterated 3-Aminophenyl(d$_3$)-piperazinyl-4-n-butyl-isobutylsulfonamide 20

A solution of 18 (0.6 g) in methanol (30 ml) was added to a mixture of tin chloride (2.2 g) and conc. HCl (6 ml) in methanol (30 ml) at −10° C. and the mixture is stirred while allowing to attain room temperature slowly. The reaction mixture is stirred for additional 24 hours at room temperature and then quenched with aqueous sodium bicarbonate solution. The mixture is extracted with dichloromethane, dried over sodium sulfate and filtered. The filtrate is concentrated in vacuo and purified by flash column chromatography to give 20 (0.45 g). Mass spectral analysis: m/e 381 (M+1).

The 3-(nitrophenyl)piperazinyl-n-butyl-isobutylsulfonamide 18 is also transformed to the amine 20 by catalytic hydrogenation of 18 using Pd/C as catalyst.

Preparation of Deuterated 3-Aminophenyl($d_3$)-piperazinyl-4-n-butyl-cyclohexylsulfonamide 21

Deuterated 3-Nitrophenyl($d_3$)-piperazinyl-4-n-butyl-cyclohexylmethylsulfonamide 19 (0.5 g) is converted to the corresponding amine 21 in a similar manner as described above for the preparation of the isobutyl analog 20. Reduction of 19 with tin chloride and conc. HCl gave 21 (0.35 g). Mass spectral analysis: m/e 425 (M+1).

SCHEME 2

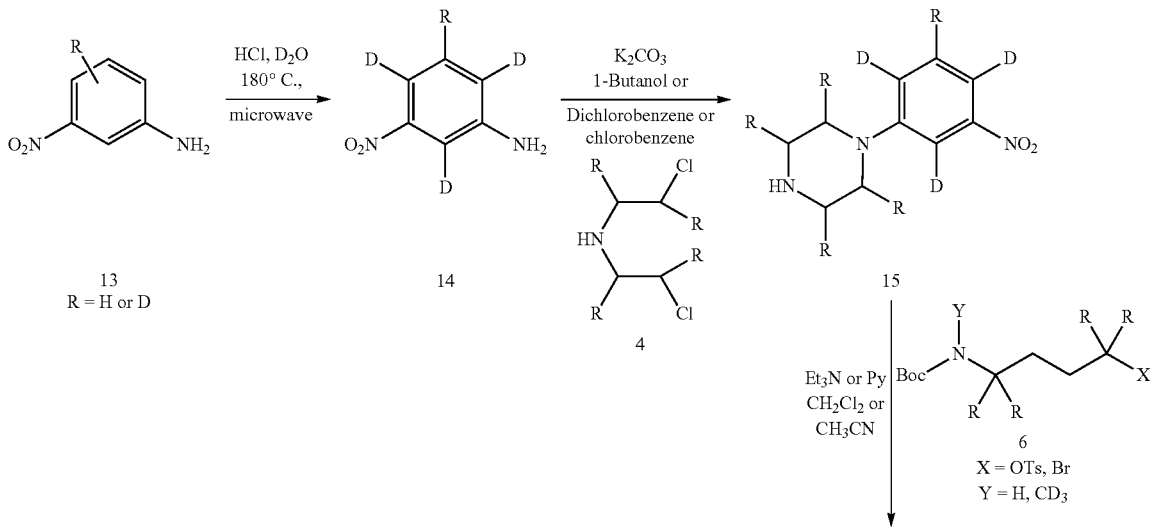

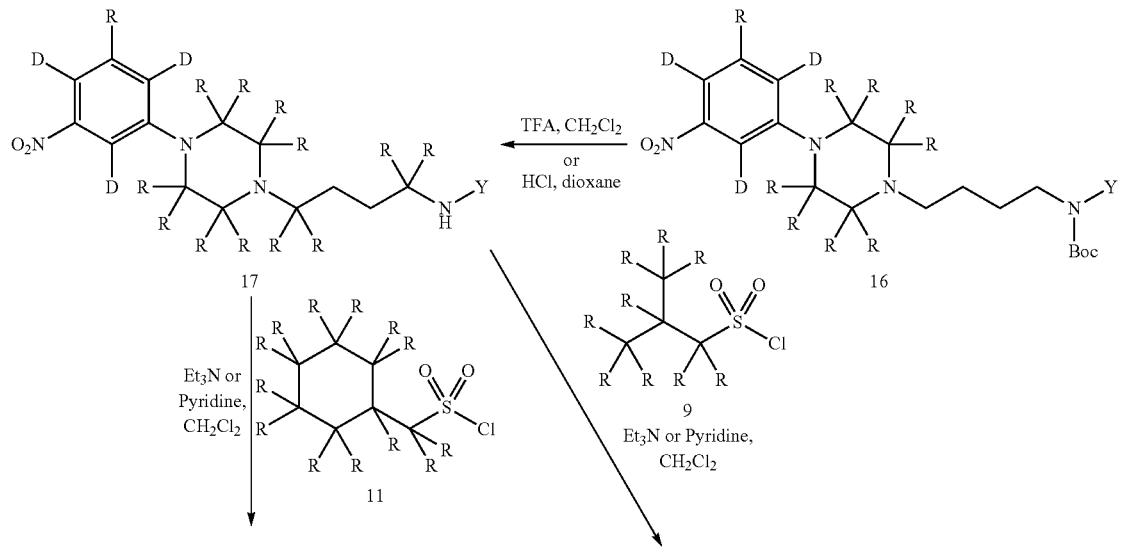

-continued

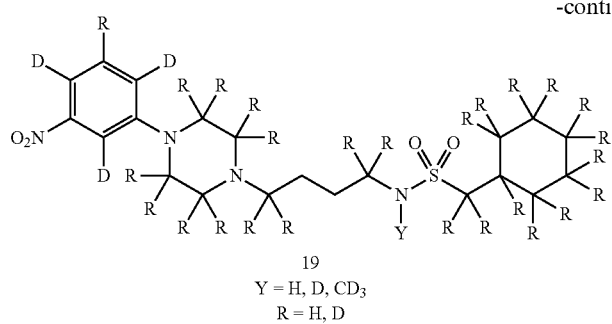

19
Y = H, D, CD₃
R = H, D

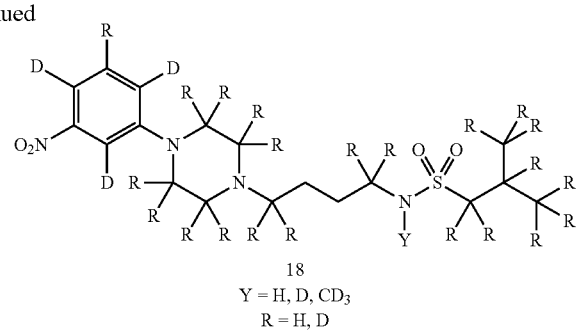

18
Y = H, D, CD₃
R = H, D

SnCl₂, HCl, MeOH, or
H₂, Pd/C, EtOH, AcOH ↓

SnCl₂, HCl, MeOH, or
H₂, Pd/C, EtOH, AcOH ↓

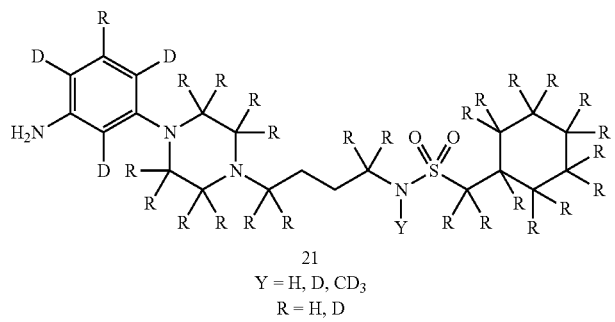

21
Y = H, D, CD₃
R = H, D

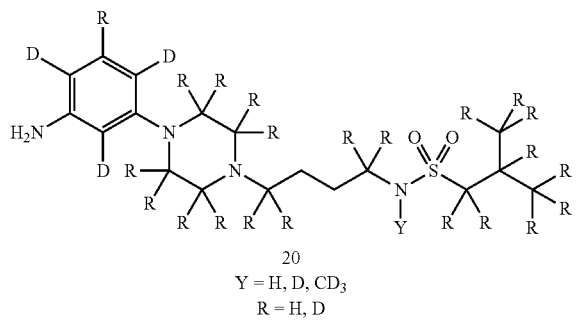

20
Y = H, D, CD₃
R = H, D

The acetylation of substituted sulfonamide anilines 20 and 21 with deuterated acetyl chloride (d₃) are illustrated in scheme 3.

Preparation of 3-(Acetylaminophenyl)piperazinyl-4-butyl)-isobutyl-sulfonamide 10

To a solution of deuterated amine 20 (0.4 g) in dichloromethane (4 ml) at 0° C. is added pyridine (1 ml), and deuterated acetyl(d₃) chloride (1 equiv) and the reaction mixture allowed to warm to room temperature and then stirred overnight. The reaction mixture is concentrated to a residue in vacuo. Dichloromethane (50 ml) is added to the residue and washed with aqueous solution of sodium bicarbonate, then brine and water. The organic phase is dried over sodium sulfate, filtered and the filtrate is concentrated in vacuo. The resulting material is purified by flash column chromatography to give the target compound, isobutyl sulfonamide, 10 (0.42 g). Mass spectral analysis: m/e 426 (M+1).

Preparation of 3-(Acetylaminophenyl)piperazinyl-4-butyl)-cyclohexylmethyl-sulfonamide 12

To a solution of deuterated amine 21 (0.3 g) in dichloromethane (4 ml) at 0° C. is added pyridine (1 ml), and deuterated acetyl(d₃) chloride (1 equiv) and the reaction mixture allowed to warm to room temperature and then stirred overnight. The reaction mixture is concentrated to a residue in vacuo. Dichloromethane (50 ml) is added to the residue and washed with aqueous solution of sodium bicarbonate, then brine and water. The organic phase is dried over sodium sulfate, filtered and the filtrate is concentrated in vacuo. The resulting material is purified by flash column chromatography to give the target compound, cyclohexylmethyl sulfonamide, 12 (0.26 g). Mass spectral analysis: m/e 470 (M+1).

The preparation of pharmaceutically acceptable salts such as deuterated-hydrochloric acid (DCl) salt is illustrated in scheme 4.

Preparation of 3-(Acetylaminophenyl)piperazinyl-4-butyl)-isobutyl-sulfonamide 10.DCl Deuterated methanol (CD₃OD) is added in excess to the sulfonamide 10 (0.28 g) and the solution stirred for 10 min under N₂ followed by addition of D₂O and HCl in ether. The volatile are removed in vacuo to give the deuterochloride (DCl) salt of 10.DCl (0.32) in which the acidic protons on the sulfonamide and amide are also exchanged for D.

Preparation of 3-(Acetylaminophenyl)piperazinyl-4-butyl)-cyclohexylmethyll-sulfonamide 12. DCl Deuterated methanol (CD₃OD) is added in excess to the sulfonamide 12 (0.25 g) and the solution stirred for 10 min under N₂ followed by addition of D₂O and HCl in ether. The volatile are removed in vacuo to give the deuterochloride (DCl) salt of 12.DCl (0.28 g) in which the acidic protons on the sulfonamide and amide are also exchanged for D.

SCHEME 3
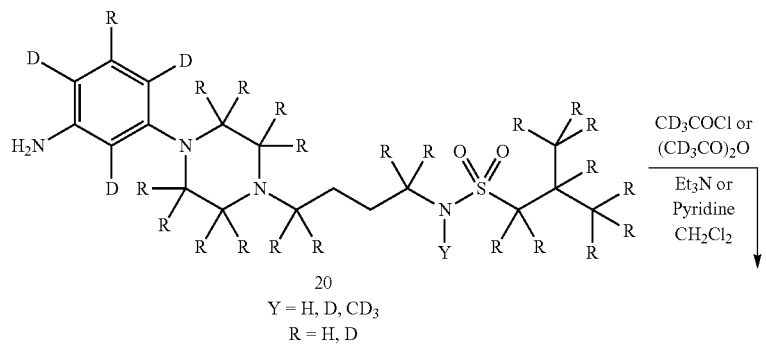
20
Y = H, D, CD₃
R = H, D
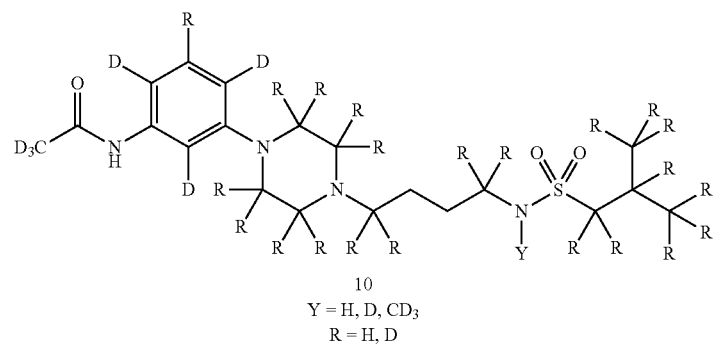
10
Y = H, D, CD₃
R = H, D
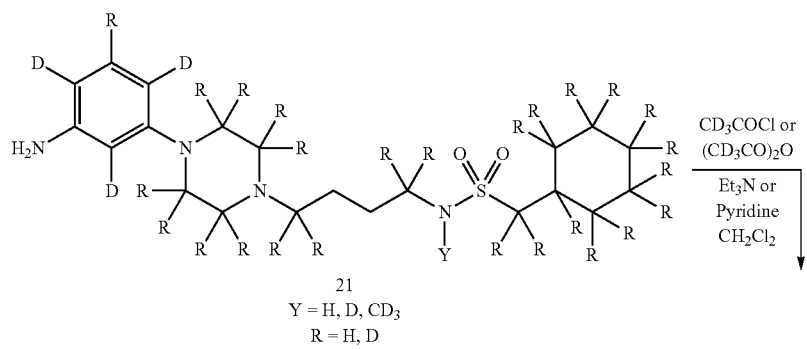
21
Y = H, D, CD₃
R = H, D
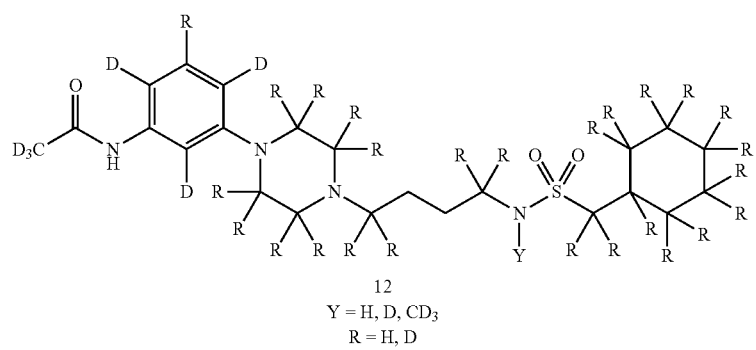
12
Y = H, D, CD₃
R = H, D

SCHEME 4

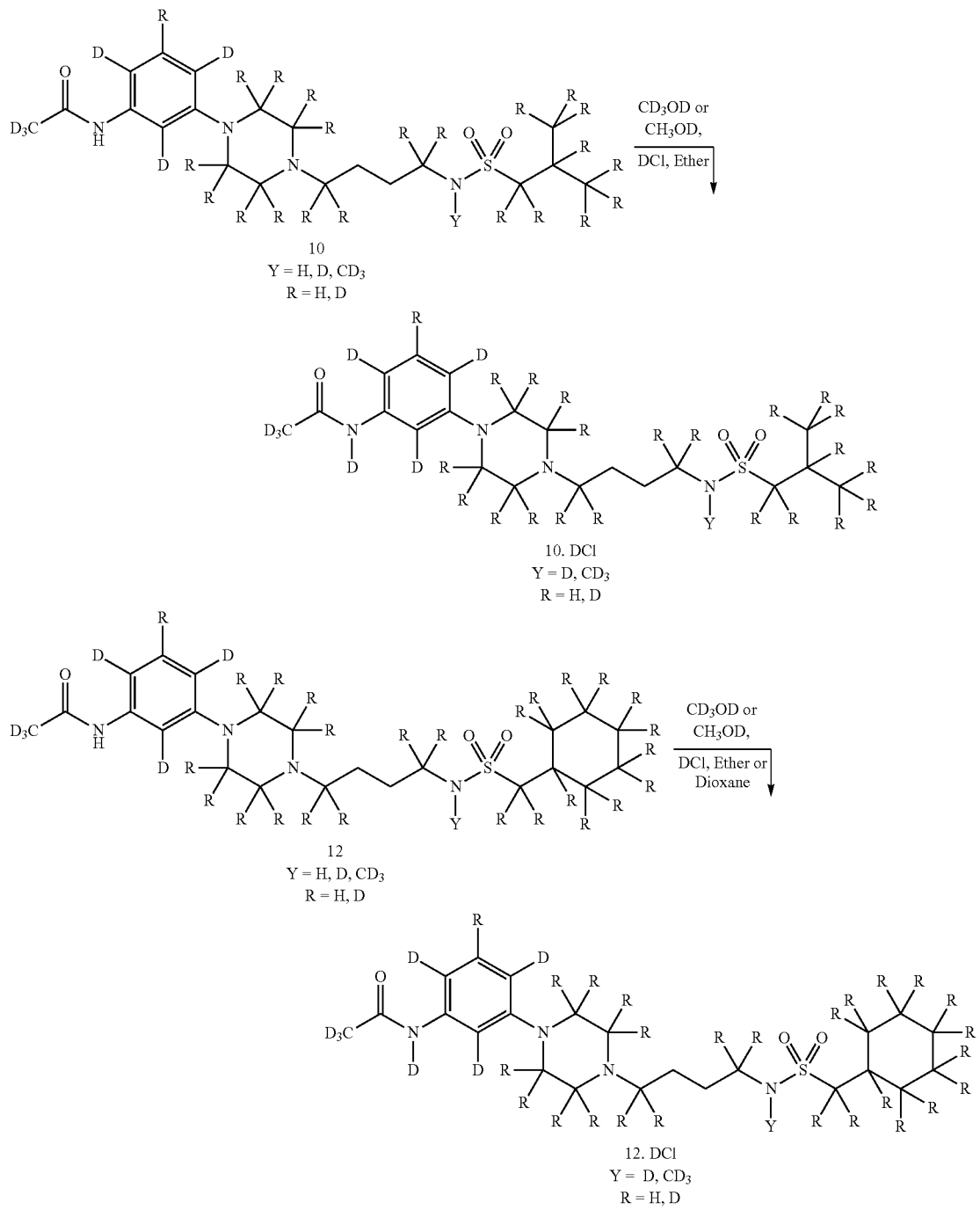

Preparation of Deuterated Isobutyl Sulfonyl Chloride 9

The deuterated isobutylsulfonyl chloride 9 is synthesized from the deuterated isobutyl alcohol (2-methylpropan-1-ol) as illustrated in Scheme 5 and described below.

To a stirred mixture of isobutyl alcohol-$d_9$ (2-methylpropan-1-ol-$d_9$) (5 g) and $CBr_4$ (1 equiv) in dichloromethane at 0° C. is added $Ph_3P$ (1 equiv) under $N_2$. The mixture is stirred for one hour and allowed to warm to room temperature with stirring for additional one hour. The reaction mixture is cooled to 0° C. and quenched with methanol. The reaction mixture is concentrated and the residue is purified by flash chromatography to yield deuterated isobutyl bromide 23 (6.2 g).

The bromide 23 (3 g) is treated with aqueous solution of sodium sulfite (3 equiv) in water for 24 hours. The reaction mixture is filtered to isolate the precipitated product 24 (2 g) which is used in the next step in which 24 it treated with thinly chloride (2 equiv) in toluene for overnite. The excess unconsumed thionyl chloride is evaporated in vacuo and the residue is diluted with ice water and extracted with ether (3×50 mL). The ether phase is washed with aqueous sodium hydrogen sulfite and then water. The ether solution is dried over calcium chloride for 30 min. The removal of calcium chloride and solvent yields deuterated isobutylsulfonyl chloride 9 (1.6 g), as an oil. Mass spectral analysis: m/e 166 (M+1).

In another method to prepare 9, the bromide 23 (5.5 g) is treated with sodium sulfide (1.1 equiv) in N,N-dimethyl formamide for 12 hours. The mixture is quenched with ice and extracted with diethyl ether. The ethereal solution is washed with 5% HCl, 10% NaHCO$_3$, brine and dried over anhydrous MgSO$_4$, filtered and concentrated in vacuo to give the deuterated isobutyl mercaptan 25 (3 g).

To the deuterated isobutyl mercaptan 25 (3 g) is added acetic acid (10 mL) and ice (3.3 g) in a 100 ml round bottom flask which is then placed in an ice bath. Chlorine gas is passed through the solution for 30 min. The reaction temperature is kept at 0° C. The reaction mixture is stirred for an additional 30 min after the Cl$_2$ addition is ceased. The reaction mixture is diluted with ice-water (30 mL) and extracted with ether. The ether extracts are combined and then washed with saturated aqueous solution of sodium hydrogen sulfite, and water. The ether solution is dried over calcium chloride for 30 min, then filtered and the filtrate is concentrated to remove the solvent to give the deuterated isobutylsulfonyl chloride 9 (4.2 g).

SCHEME 5

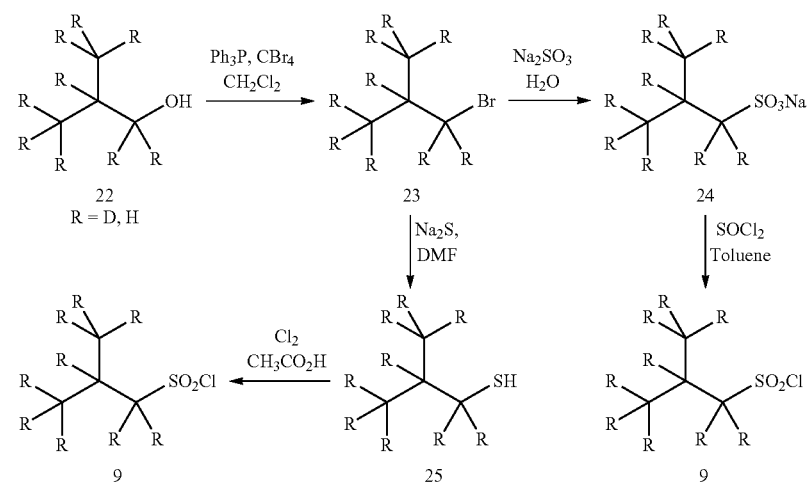

The deuterated cyclohexylmethyl sulfonyl chloride 11 is prepared as illustrated in scheme 6 below from the corresponding deuterated cyclohexylmethyl alcohol 26 using the methods as described above for the preparation of deuterated isobutylsulfonyl chloride 9 in scheme 5.

SCHEME 6

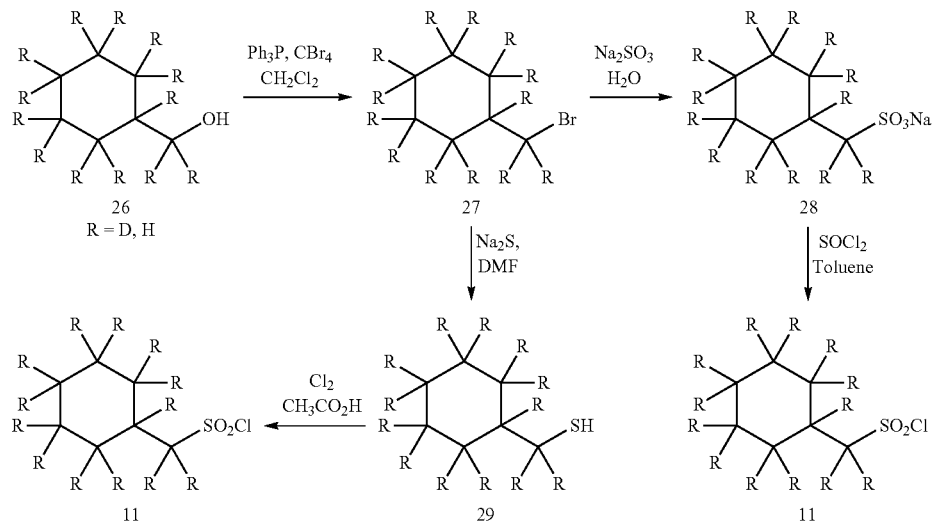

TABLE 1
Given below are compounds that are representative examples of the present invention.
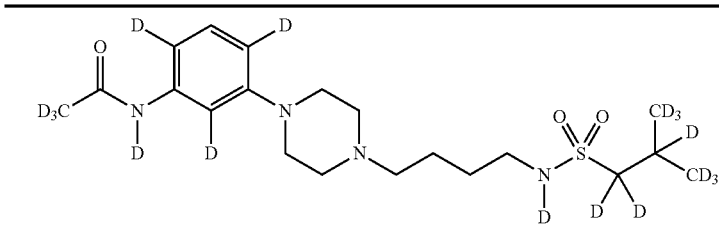
1
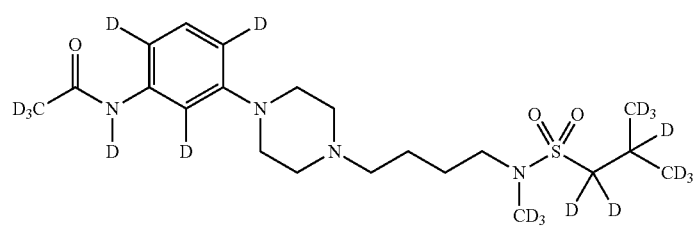
2
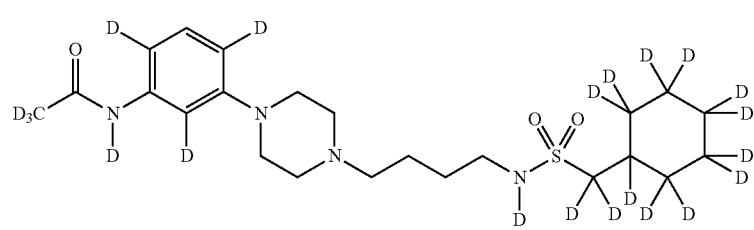
3
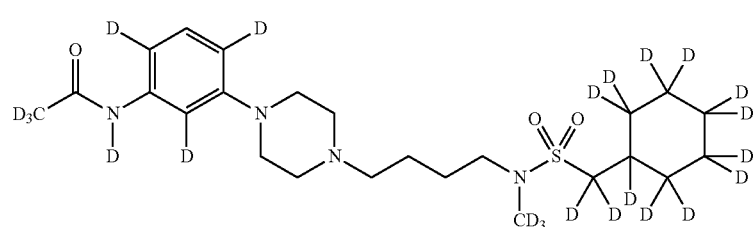
4
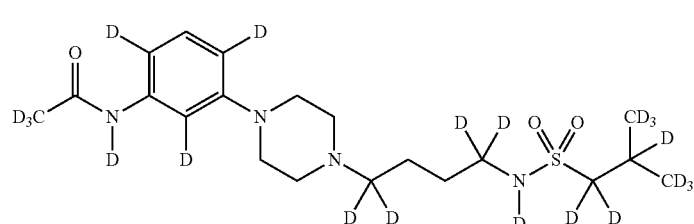
5
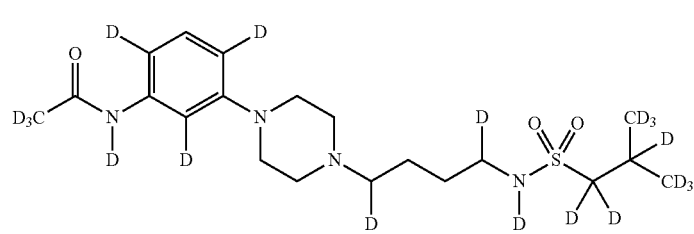
6
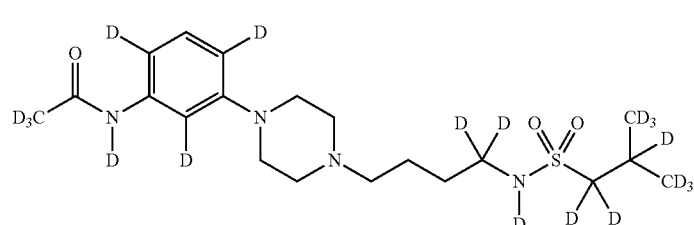
7

TABLE 1-continued
Given below are compounds that are representative examples of the present invention.
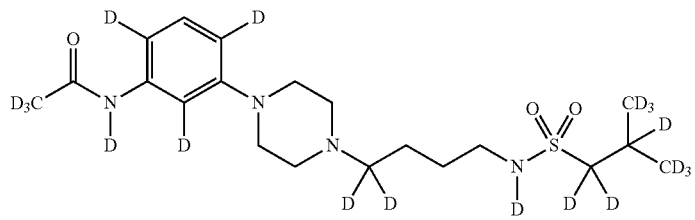
8
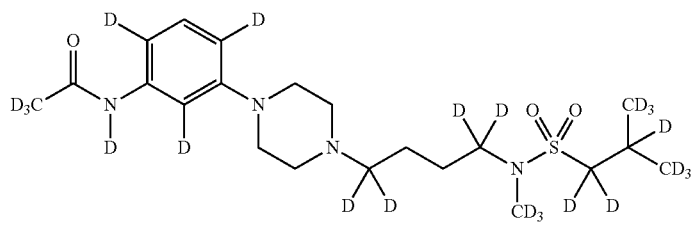
9
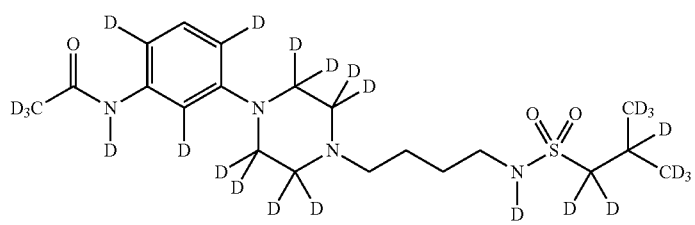
10
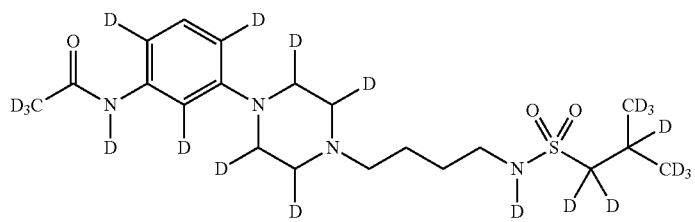
11
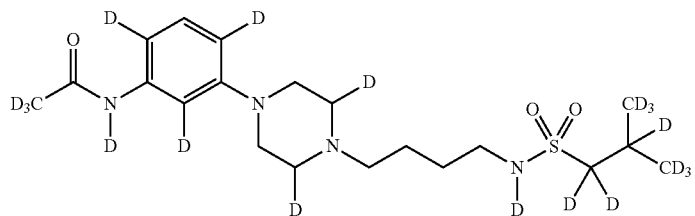
12
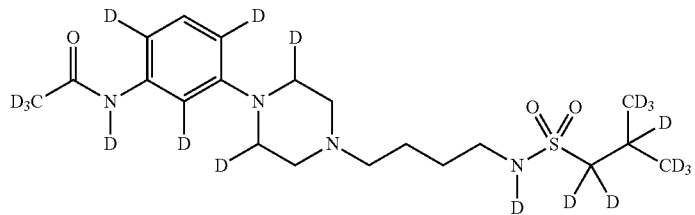
13
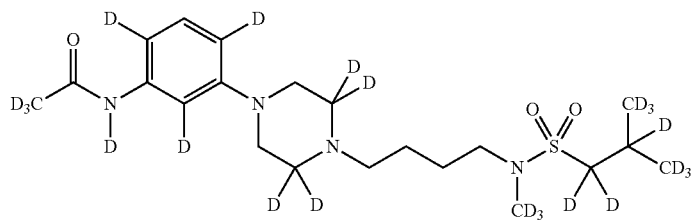
14

TABLE 1-continued
Given below are compounds that are representative examples of the present invention.
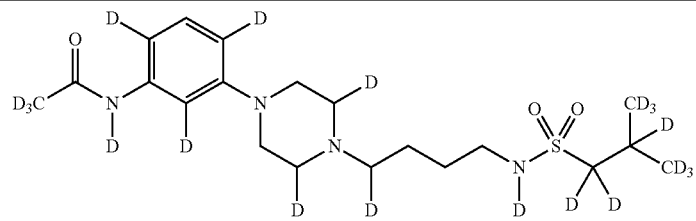
15
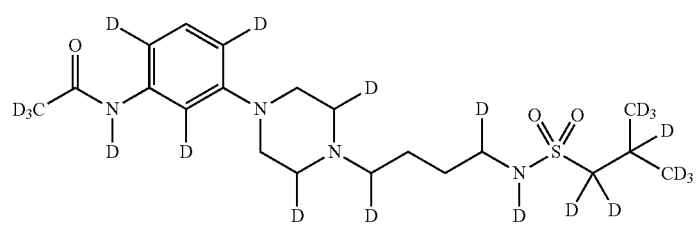
16
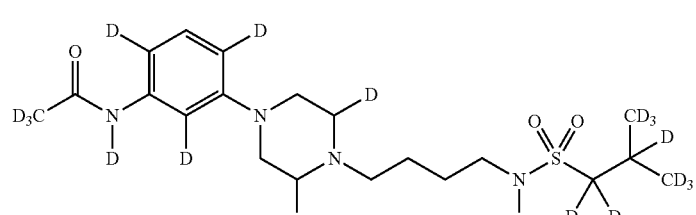
17
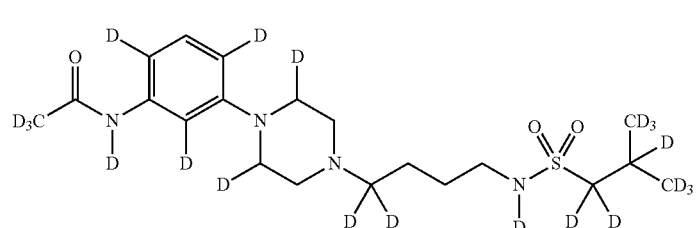
18
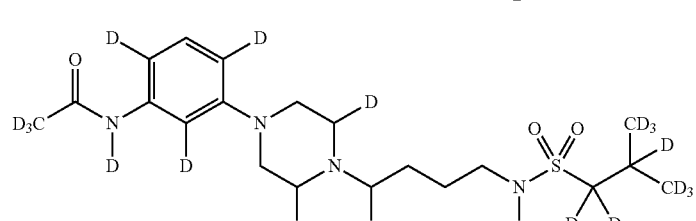
19
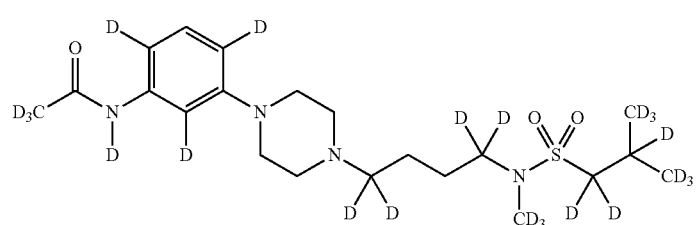
20
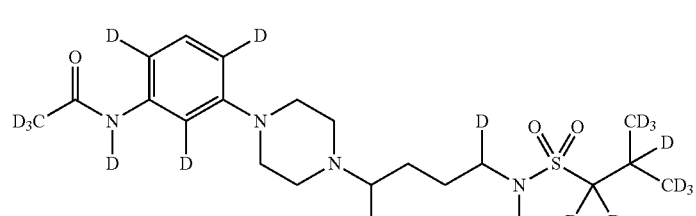
21

TABLE 1-continued

Given below are compounds that are representative examples of the present invention.

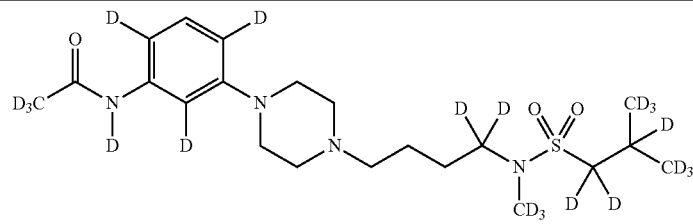

22

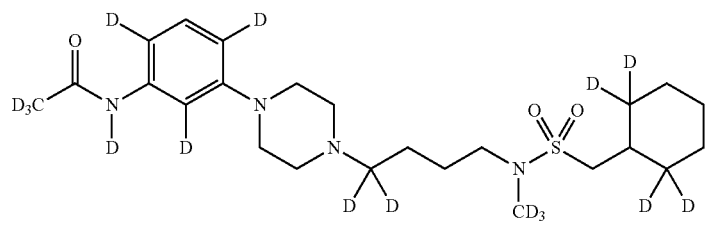

23

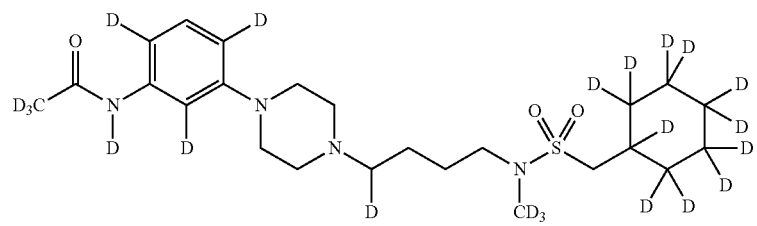

24

33
-continued
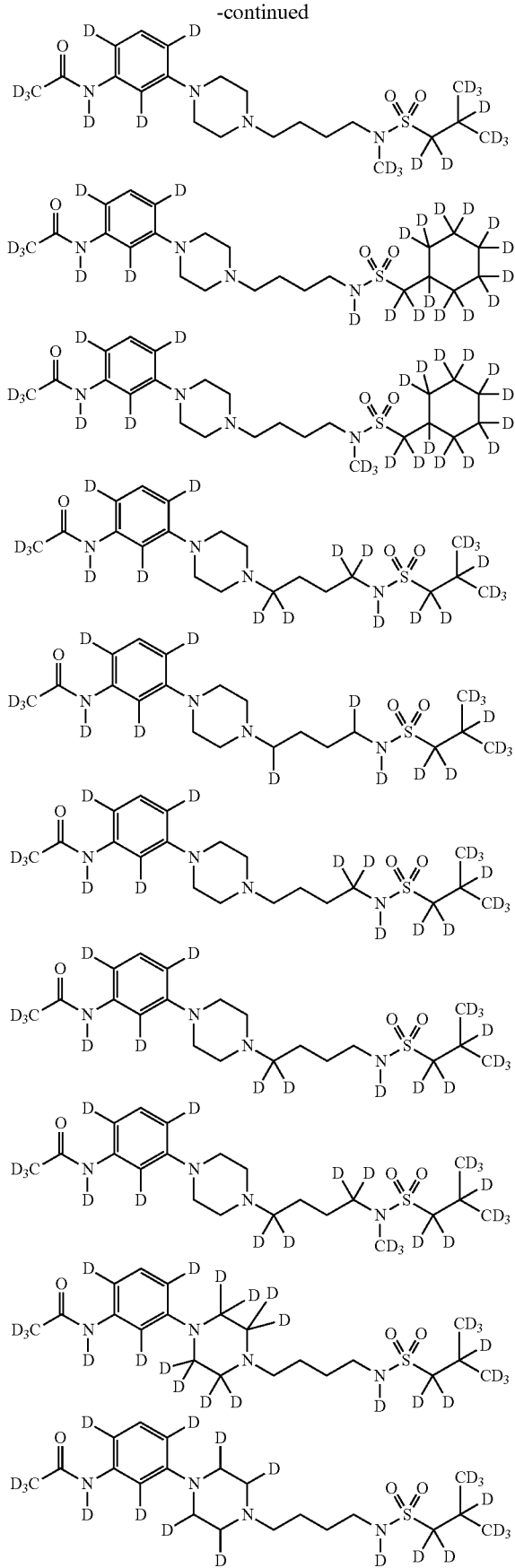
34
-continued
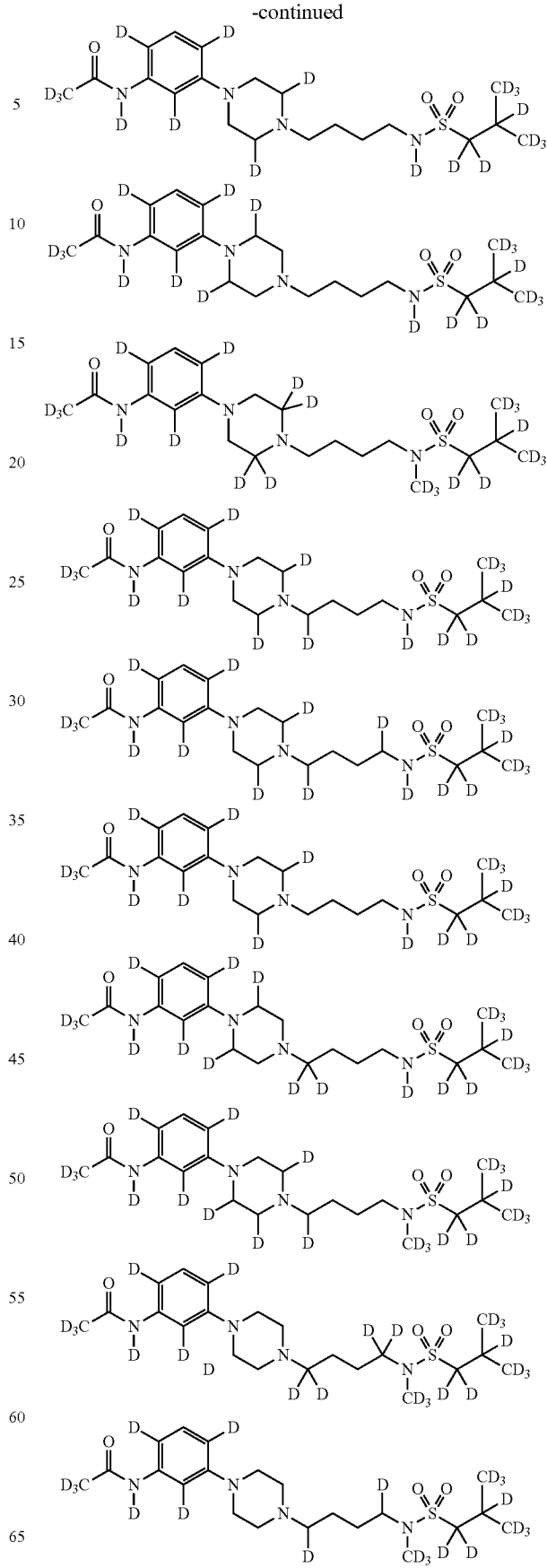

-continued
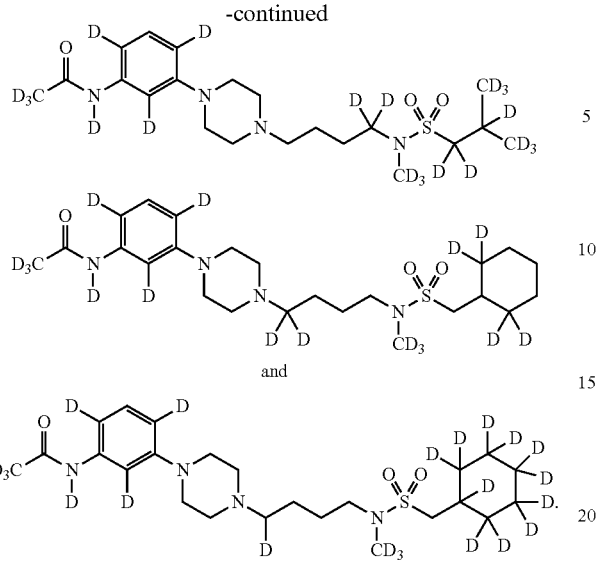

What is claimed is:

1. A deuterium-enriched compound of formula I and II, or the pharmaceutically acceptable salt thereof, wherein:

$R_1$-$R_{34}$ of formula I are independently selected from H and D;

$R_1$-$R_{38}$ of formula II are independently selected from H and D;

$R_{25}$ in both formula I and II is independently selected from H, D and $CD_3$;

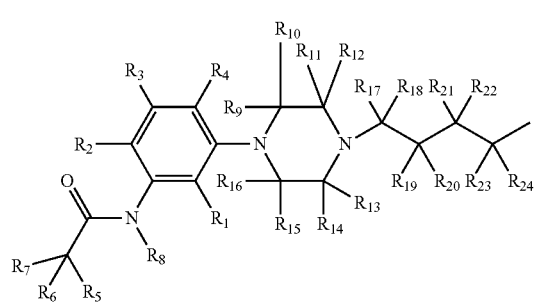

I

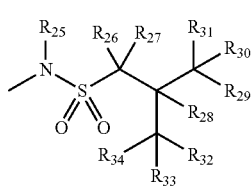

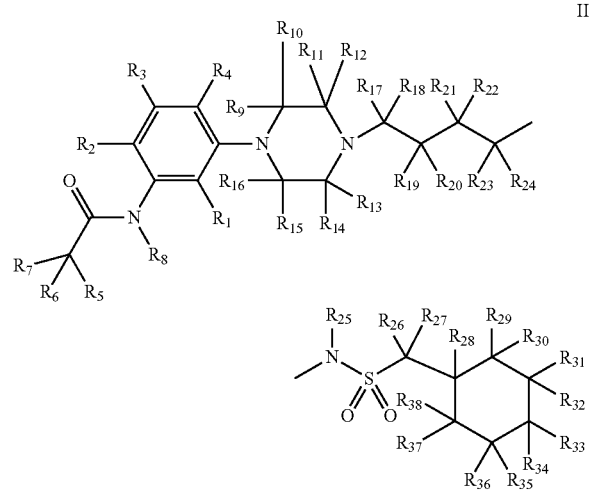

II and the abundance of deuterium in compounds of formula I or formula II is at least 1%, 2%, 3%, 4%, 5%, 6%, 7%, 3%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 545, 55%, 56%, 57%, 58%, 59%, 60%, 61%, 62%, 63%, 64%, 65%, 66%, 67%, 68%, 69%, 70%, 71%, 72%, 73%, 74%, 755, 76%, 77%, 78%, 79%, 80%, 81%, 81%, 83%, 84%, 85%, 86%, 87%, 88%, 89%, 90%, 91%, 92%, 93%, 94%, 95%, 96%, 97%, 98%, 99% and 100%.

2. A deuterium-enriched compound of claim 1 selected from the group consisting of:

Deuterated N-3-(Acetyl($d_3$)amino($d_1$)phenyl($d_3$)-1-piperazinyl-4-n-butyl)-isobutyl($d_9$)-sulfonamide(N-$d_1$), deuterium chloride (2DCl);

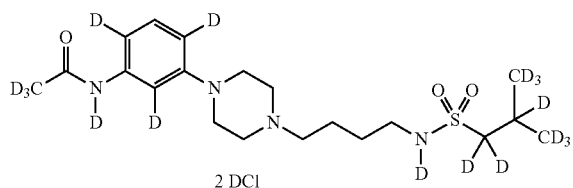

2 DCl

Deuterated N-3-(Acetyl($d_3$)amino($d_1$)phenyl ($d_3$)-1-piperazinyl-4-n-butyl)-isobutyl($d_9$)-N-methyl($d_3$)-sulfonamide, deuterium chloride (2DCl);

2 DCl

Deuterated N-3-(Acetyl($d_3$)amino($d_1$)phenyl ($d_3$)-1-piperazinyl-4-n-butyl)-cyclohexylmethyl($d_{13}$)-sulfonamide (N-$d_1$), deuterium chloride (2DCl);

2 DCl

Deuterated N-3-(Acetyl($d_3$)amino($d_1$)phenyl ($d_3$)-1-piperazinyl-4-n-butyl)-cyclohexylmethyl($d_{13}$)-N-methyl ($d_3$)-sulfonamide, deuterium chloride (2DCl);

2 DCl and the pharmaceutically acceptable salts thereof.

3. The deuterium enriched compound of claim 1, wherein the deuterium-enriched compound is N-3-(Acetyl($d_3$)amino($d_1$)phenyl ($d_3$)-1-piperazinyl-4-n-butyl)-isobutyl($d_9$)-sulfonamide (N-$d_1$), deuterium chloride (2DCl) salt, 2 DCl 4. The deuterium enriched compound of claim 1, wherein the deuterium-enriched compound is N-3-(Acetyl($d_3$)amino($d_1$)phenyl ($d_3$)-1-piperazinyl-4-n-butyl) isobutyl($d_9$)-N-methyl($d_3$)sulfonamide, deuterium chloride (2DCl) salt, 2 DCl 5. The deuterium enriched compound of claim 1, wherein the deuterium-enriched compound is N-3-(Acetyl($d_3$)amino($d_1$)phenyl ($d_3$)-1-piperazinyl-4-n-butyl)-cyclohexylmethyl($d_{13}$)-sulfonamide (N-$d_1$), deuterium chloride (2DCl) salt, 2 DCl 6. The deuterium enriched compound of claim 1, wherein the deuterium-enriched compound is N-3-(Acetyl($d_3$)amino($d_1$)phenyl ($d_3$)-1-piperazinyl-4-n-butyl)-cyclohexylmethyl($d_{13}$)-N-methyl($d_3$)-sulfonamide, deuterium chloride (2DCl) salt, 2 DCl 7. A deuterium enriched compound of claim 1, or the pharmaceutically acceptable salts thereof wherein a compound is selected from the group consisting of: